(12) United States Patent
Johnson

(10) Patent No.: US 7,270,541 B1
(45) Date of Patent: Sep. 18, 2007

(54) ENDODONTIC FILES HAVING VARIABLE HELICAL ANGLE FLUTES

(76) Inventor: William B. Johnson, 2727 E. 21st St., Suite 500, Tulsa, OK (US) 74114

(*) Notice: Subject to any disclaimer, the term of this patent is extended or adjusted under 35 U.S.C. 154(b) by 0 days.

(21) Appl. No.: 11/366,059

(22) Filed: Mar. 2, 2006

(51) Int. Cl.
  *A61C 5/02* (2006.01)
(52) U.S. Cl. ..................................... 433/102
(58) Field of Classification Search ................. 433/102
  See application file for complete search history.

(56) References Cited

U.S. PATENT DOCUMENTS

| | | | |
|---|---|---|---|
| 4,443,193 A | 4/1984 | Roane | |
| 4,536,159 A | 8/1985 | Roane | |
| 4,934,934 A | 6/1990 | Arpaio, Jr. et al. | |
| RE34,439 E | 11/1993 | Heath | |
| 5,380,200 A | 1/1995 | Heath et al. | |
| 5,464,362 A | 11/1995 | Heath et al. | |
| 5,503,554 A | 4/1996 | Schoeffel | |
| 5,658,145 A | 8/1997 | Maillefer et al. | |
| 5,676,541 A | 10/1997 | Maillefer et al. | |
| 5,692,902 A | 12/1997 | Aeby | |
| 5,873,719 A | 2/1999 | Calas et al. | |
| 5,882,198 A * | 3/1999 | Taylor et al. | 433/102 |
| 5,897,316 A | 4/1999 | Buchanan | |
| 5,921,775 A * | 7/1999 | Buchanan | 433/102 |
| 5,975,899 A | 11/1999 | Badoz et al. | |
| 6,012,921 A | 1/2000 | Riitano | |
| 6,074,209 A | 6/2000 | Johnson | |
| 6,206,695 B1 * | 3/2001 | Wong et al. | 433/102 |
| 6,217,335 B1 | 4/2001 | Riitano et al. | |
| 6,267,592 B1 | 7/2001 | Mays | |
| 6,312,261 B1 | 11/2001 | Mays | |
| 6,315,558 B1 | 11/2001 | Farzin-Nia et al. | |
| 6,390,819 B2 | 5/2002 | Riitano | |
| 6,419,488 B1 | 7/2002 | McSpadden et al. | |
| 6,514,076 B1 | 2/2003 | Bleisweiss et al. | |
| 6,520,774 B1 | 2/2003 | Mays | |
| 6,644,972 B1 | 11/2003 | Mays | |
| 6,746,245 B2 | 6/2004 | Riitano et al. | |
| 2003/0077553 A1 | 4/2003 | Brock | |
| 2004/0023186 A1 | 2/2004 | McSpadden | |
| 2004/0043357 A1 | 3/2004 | Garman | |
| 2004/0058297 A1 | 3/2004 | Danger | |
| 2004/0121283 A1 * | 6/2004 | Mason | 433/102 |
| 2004/0191723 A1 * | 9/2004 | Shearer et al. | 433/102 |
| 2005/0282108 A1 * | 12/2005 | Goodis | 433/102 |

* cited by examiner

*Primary Examiner*—Cary E. O'Connor
(74) *Attorney, Agent, or Firm*—Gable Gotwals

(57) ABSTRACT

A rotatable endodontic file for cleaning/shaping a tooth root canal, comprising an elongated shaft having a proximal end portion, a distal end and a tapered working portion having a rotational axis, the working portion extending from the proximal portion to the distal end, the external surface of the shaft working portion having a plurality of at least two spiraled, spaced apart continuous helical flutes, the flutes having therebetween an equal number of spiraled, spaced apart flanges, each flange having in a plane perpendicular the rotational axis an outer end surface forming a continuous spiraled scraping/cutting edge extending the length of the shaft working portion, the flutes having helical angles relative to the rotational axis of between 10° and 30° and wherein the helical angles vary at selected longitudinal locations.

7 Claims, 3 Drawing Sheets

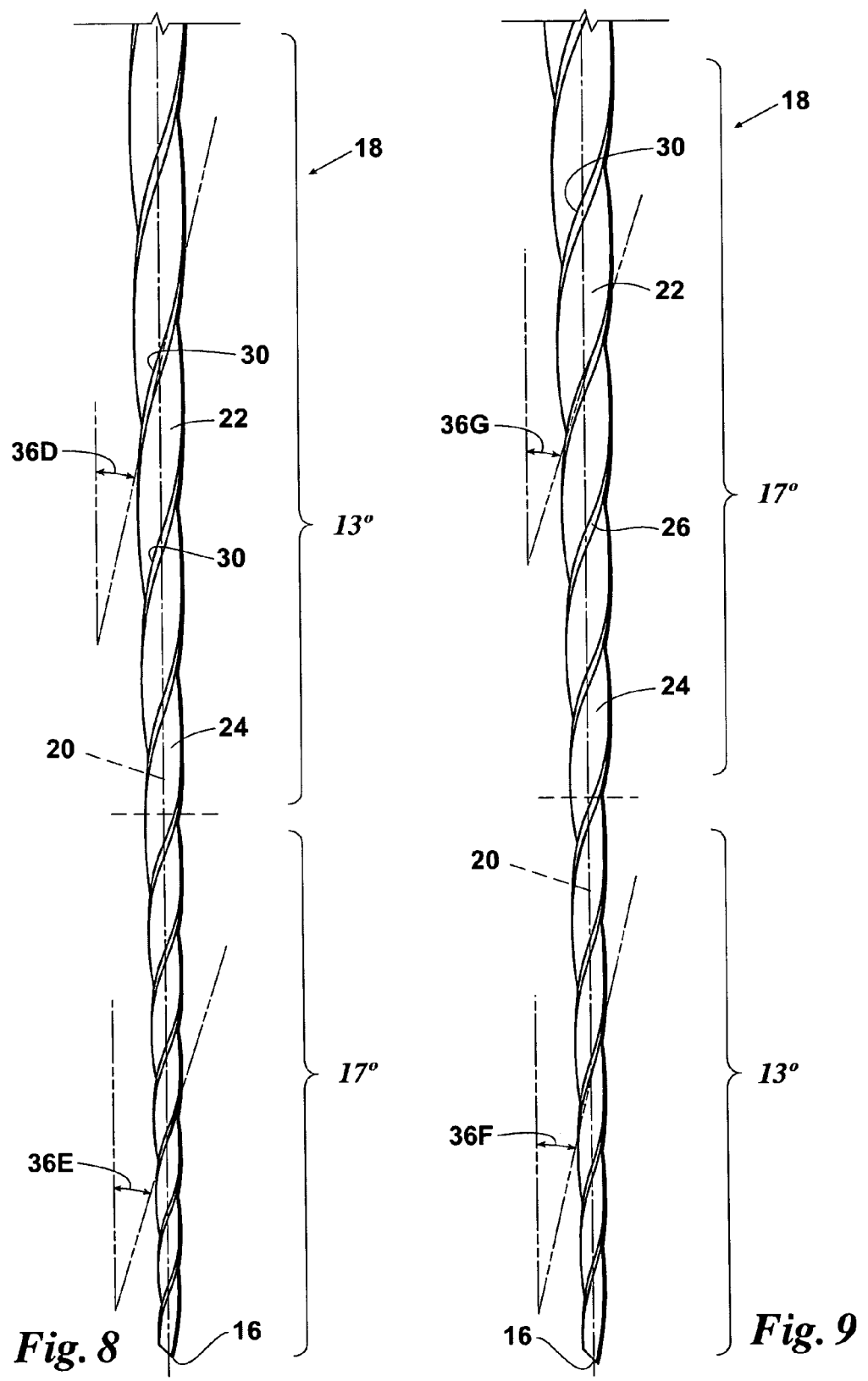

ENDODONTIC FILES HAVING VARIABLE HELICAL ANGLE FLUTES

REFERENCE TO PENDING APPLICATIONS

This application is not based upon any pending domestic or international patent applications.

REFERENCE TO MICROFICHE APPENDIX

This application is not referenced in any microfiche appendix.

BACKGROUND OF THE INVENTION

1. Field of the Invention

The present invention relates generally to endodontic files and more particular to root canal files or reamers used in the cleaning of material present in the root canal of human teeth and for enlarging and shaping the root canal so that it is prepared for receiving filling material.

2. Description of the Related Art

A great improvement in the dental profession in the last half century has been in the field of endodontics, that is, the treatment of abscessed teeth by treatment of the tooth root canal. A relatively, but yet difficult dental procedure is that of cleaning, shaping and filling the root canal of a patient's tooth. In the performance of the root canal procedure typically a hole is first drilled in the crown or the exposed portion of the tooth. The hole drilled through the crown provided access to the interior of the tooth and specifically access to the tooth root canal or root canals. In order to treat the tooth, the canal or canals must be thoroughly cleaned of pulpal material that, in the case of an abscessed tooth, is typically infected. The technician or dental practitioner must remove this pulpal material to alleviate the infection. Next the technician or dental practitioner must clean and shape the root canal so that it can be effectively filled with a filler material, such as gutta percha.

Much work has been done on the instrumentation need for effective treatment of root canals. Root canals are typically treated with endodontic files. The term "file" as used in this patent application means an elongated device insertable into a root canal and that can be manipulated either manually or by machine, to clean and shape the root canal. Thus a dental file serves two basic purposes. First it serves to remove pulpal material from the interior of the tooth. Second it serves to shape the tooth root canal so that it can be more effectively filled. Thus, in addition to the cleaning function, a typical dental file serves also as a reamer, that is, a device to enlarge and shape the canal. In this application, the term "file" is intended to mean a "reamer/file" since it functions not only to clean a root canal of pulpal material but also to shape or ream the root canal.

For background information relating to endodontic files of the type that is the subject of this patent application, reference may be had to the following issued United States patents and publications:

| U.S. Pat. No. | INVENTOR(S) | ISSUE DATE | TITLE |
| --- | --- | --- | --- |
| 4,443,193 | Roane | Apr. 17, 1984 | Endodontic Instrument |
| 4,536,159 | Roane | Aug. 20, 1985 | Endodontic Instrument |
| 4,934,934 | Arpaio, Jr. et al. | Jun. 19, 1990 | Dental File/Reamer Instrument |
| 5,380,200 | Heath et al. | Jan. 10, 1995 | Endodontic Instrument Of Predetermined Flexibility |
| 5,464,362 | Heath et al. | Nov. 7, 1995 | Endodontic Instrument |
| 5,503,554 | Schoeffel | Apr. 2, 1196 | Endodontic Files |
| 5,658,145 | Maillefer et al. | Aug. 19, 1997 | Set Of Instruments For Boring Dental Radicular Canals And Method Therefor |
| 5,676,541 | Maillefer et al. | Oct. 14, 1997 | Set of Instruments Of Increasing Dimension For The Boring Of Radicular Dental Canals |
| 5,692,902 | Aeby | Dec. 2, 1997 | Set Of Instruments For The Boring Of Radicular Dental Canals |
| 5,873,719 | Calas et al. | Feb. 23, 1999 | Dental Reamer |
| 5,897,316 | Buchanan | Apr. 27, 1999 | Endodontic Treatment System |
| 5,921,775 | Buchanan | Jul. 13, 1999 | Endodontic Treatment System |
| 5,975,899 | Badoz et al. | Nov. 2, 1999 | Dental Reamer |
| 6,012,921 | Riitano | Jan. 11, 2000 | Endodontic Systems For The Anatomical, Sectional And Progressive Corono-Apical Preparation Of Root Canals With Three Sets Of Dedicated Instruments |
| 6,074,209 | Johnson | Jun. 13, 2000 | Reduced Torque Endodontic File |
| 6,217,335 | Riitano et al. | Apr. 17, 2001 | Endodontic Systems And Methods For The Anatomicall, Sectional And Progressive Corono-Apical Preparation Of Root Canals With Minimal Apical Intrusion |
| 6,267,592 | Mays | Jul. 31, 2001 | Highly Flexible Instrument For Dental Applications |
| 6,312,261 | Mays | Nov. 6, 2001 | Endodontic Obturator With Removable Carrier And Method Of Use Thereof |
| 6,315,558 | Farzin-Nia et al. | Nov. 13, 2001 | Method Of Manufacturing Superelastic Endodontic Files And Files Made Therefrom |
| 6,390,819 | Riitano | May 21, 2002 | Endodontic Systems And Methods For The Anatomical, Sectional And Progressive Corono-Apical Preparation Of Root Canals With Dedicated Stainless Steel Instruments And Dedicated Nickel/Titanium Instruments |
| 6,419,488 | McSpadden et al. | Jul. 16, 2002 | Endodontic Instrument Having A Chisel Tip |

-continued

| U.S. Pat. No. | INVENTOR(S) | ISSUE DATE | TITLE |
| --- | --- | --- | --- |
| 6,514,076 | Bleiweiss et al. | Feb. 4, 2003 | Precipitation Hardenable Stainless Steel Endodontic Instruments And Methods For Manufacturing And Using The Instruments |
| 6,520,774 | Mays | Feb. 18, 2003 | Highly Flexible Instrument For Medical Applications |
| 6,644,972 | Mays | Nov. 11, 2003 | Endodontic Obturator With Removable Carrier And Method Of Use Thereof |
| 6,746,245 | Riitano et al. | Jun. 8, 2004 | Methods For Cleaning And Shaping Asymmetrical Root Canals In An Anatomical Fashion |
| 2004/0121283 | Mason | Jun. 24, 2004 | Precision Cast Dental Instrument |
| 2003/0077553 | Brock | Apr. 24, 2003 | Endodontic Instrument Having Notched Cutting Surfaces |
| 2004/0058297 | Danger | Mar. 2, 2004 | Root Canal Instrument |
| 2004/0043357 | Garman | Mar. 4, 2004 | Endodontic Instrument |
| 2004/0023186 | McSpadden | Feb. 5, 2004 | Multi-Tapered Endodontic File |
| Re. 34,439 | Heath | Nov. 9, 1993 | Dental Compactor Instrument |

BRIEF SUMMARY OF THE INVENTION

The invention herein relates to endodontic files having variable helical angle flutes. The file of this invention is for cleaning and/or shaping a root canal of a human tooth. The improved file is in the form of an elongated shaft having a proximal end portion, a distal end and a tapered working portion having a rotational axis, the working portion extending from the proximal portion to the distal end. The external surface of the shaft working portion has a plurality of at least two spiraled, equally spaced apart, continuous concave helical flutes. The spaced apart flutes have a concave flute surfaces. The flute surfaces have therebetween an equal number of spiraled, spaced apart, continuous flanges. Each flange has, in a plane perpendicular the rotational axis, an outer end surface forming a continuous spiral scraping/cutting edge. The scraping/cutting edge extends the length of the shaft working portion.

The flutes have helical angles relative to the rotational axis. The angle of the helical flutes can vary between about 10° and about 30°. In preferred embodiments, the helical angle can typically vary between 10° and 20°.

The shaft working portion is typically tapered from a larger diameter adjacent the proximal end portion to a small diameter adjacent the distal end. In some files, the helical angle varies in proportion to the cross-sectional diameter of the shaft working portion.

In short, a typical endodontic file in use today has flutes with consistent helical angles, the consistency being in one case where the same helical angle exists from one end to the other of the tapered working portion or in the case where the helical angle varies in proportion to the diameter of the file. Further, the file can have an outer end surface of each flange that in one area provides a positive scraping/cutting edge and in another area a negative scraping/cutting edge. An important aspect of the invention herein is the provision wherein the helical angle of the flute is selectably varied at selected areas along the length of the file to thereby vary the characteristics of the file.

Most passive files have helical angles that are constant from the tip to the top of the shaft. In the smaller sizes this presents few problems. However, in sizes above 30 or 35 hundredths of a millimeter tip diameter the surface area of the radial lands in contact with the root canal sidewall is so great the file has a tendency to self-thread or pull into the canal. By reducing the helical angle the surface area of the radial lands in contact with the root canal sidewall is reduced and slippage of the rotating file occurs reducing the feed rate of the file into the canal.

In an additional embodiment, the invention is in the form of a plurality of sets of endodontic files wherein all of the files in each set have essentially the same helical angle and wherein different sets have variable diameters and/or tapers.

A better understanding of the invention will be obtained from the following detailed description of the preferred embodiments and claims, taken in conjunction with the attached drawings.

BRIEF DESCRIPTION OF THE DRAWINGS

FIG. 1 illustrates an example of a machine manipulated file.

FIG. 5 illustrates a file primarily designed for scraping action within the root canal rather than a coring or cutting action. The design of FIG. 5 is primarily for shaping a root canal and has limited ability to remove material from within the root canal.

FIGS. 6 and 7 illustrate the fact that files of the same diameter and same taper can have different helical angles.

FIG. 8 shows the external surface of the working portion of an endodontic file having a plurality of spiraled equally spaced apart continuous concaved helical flutes, the flutes having therebetween an equal number of spiraled, spaced apart continuous flanges, and wherein the flanges have in one portion of the file intermediate the file proximal end and distal end have an angle relative to a plane of the longitudinal/rotational axis of 13°, and wherein another portion of the shaft working portion adjacent the distal end has helical flutes and helical flanges having a helical angle with respect to a plane of the file longitudinal/rotational axis of 17°, illustrating the fact that the helical angle can selectably vary along the length of the file working portion.

FIG. 9, like FIG. 8, shows an external view of a portion of the shaft working portion having a plurality of at least two spaced spiraled continuous helical flutes with spiraled, spaced apart, continuous flanges therebetween and wherein in the intermediate portion of the length of the shaft working portion the flanges have an angle with respect to a plane of the longitudinal/rotational axis of 17° while the portion of the shaft working portion adjacent the distal end provides spiral flanges having an angle with respect to a plane of the longitudinal/rotational axis of 13°.

DETAILED DESCRIPTION OF THE PREFERRED EMBODIMENTS

Figure 1:
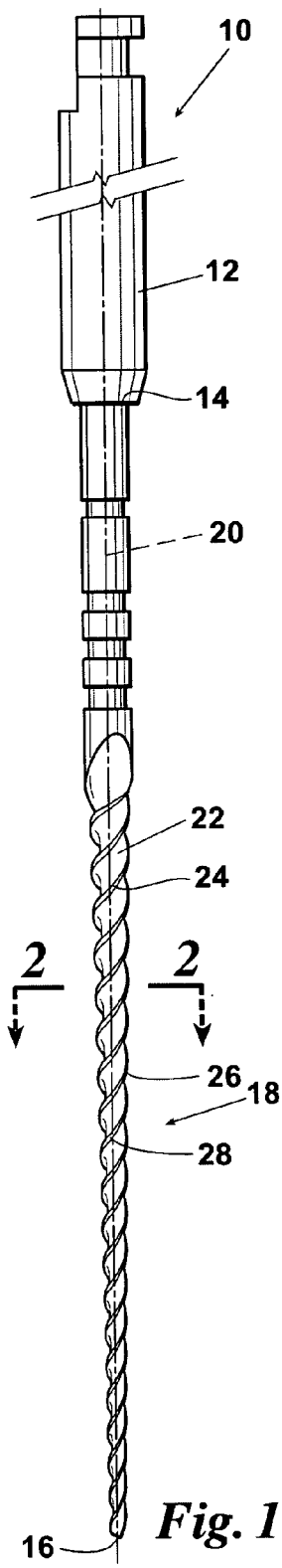
FIG. 1 is an elevational external view of a typical endodontic file. The file illustrated in this figure is for use in a hand piece by which the endodontic file is mechanically rotated and by which the file can be manipulated in the root canal of a patient. Basically, endodontic files are of two types, that is, manually manipulated and machine manipulated.

It is to be understood that the invention that is now to be described is not limited in its application to the details of the construction and arrangement of the parts illustrated in the accompanying drawings. The invention is capable of other embodiments and of being practiced or carried out in a variety of ways. The phraseology and terminology employed herein are for purposes of description and not limitation.

Elements illustrated in the drawings are identified by the following numbers:

| | |
|---|---|
| 10 | Endodontic file |
| 12 | Chuck stem |
| 14 | Proximal end |
| 16 | Distal end |
| 18 | Shaft working portion |
| 20 | Longitudinal/rotational axis |
| 22 | flute |
| 24 | Flute surface |
| 26 | Flange |
| 28 | Flange end surface |
| 30 | Scraping/cutting edge |
| 32 A-D | Planar end surfaces |
| 34 A-B | Scraping edges |
| 36 A-F | Helical angle |

Referring to the drawings and first to FIG. 1, an endodontic file is indicated generally by the numeral 10. The file includes a chuck stem 12 that is at a proximal end 14 of the file. The distal end 16 is of substantially reduced diameter compared to the proximal end. Between proximal end 14 and distal end 16 is an elongated shaft working portion generally indicated by the numeral 18.

Chuck stem 12 is typically integrally formed with the metal file and is configured to be received in a chuck (not shown) of a dental hand piece by which the file is rotated and by which the file can be manipulated in and out of a root canal by an endodontist. Chuck stem 12 can be replaced by a small plastic handle portion configured for manual manipulation by an endodontic practitioner. Whether a chuck stem or a handle portion is used is irrelevant to the invention herein and the specific configuration of chuck stem 12 is not part of the invention. Instead, an important aspect of the present invention is the configuration of the external surface of the file shaft working portion 18. Exemplary cross-sectional configurations are illustrated in the cross-sectional views of FIGS. 2, 3 and 4.

Figure 2:
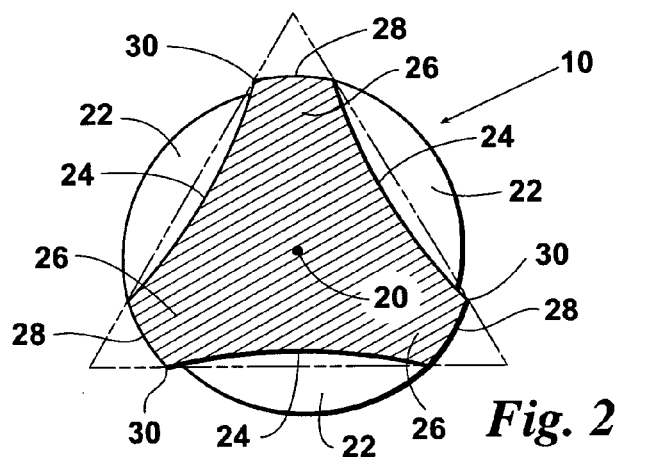
FIG. 2 is a cross-sectional view of the endodontic file of FIG. 1 taken along the line 2-2 of FIG. 1. The cross-sectional view is perpendicular the longitudinal/rotational axis of the file and illustrates a geometry having essentially passive cutting/scraping action.

FIG. 2 is a cross-sectional view taken along the line 2-2 of FIG. 1. The plane of this cross-sectional view is perpendicular to a longitudinal axis 20 of the file working portion 18 which also is the longitudinal axis of the chuck stem 12. This longitudinal axis can also be termed a rotational axis as it is the axis about which file working portion 18 is rotated when positioned within a tooth root canal. Rotational axis 20 is seen in each of the cross-sectional views.

Formed on the exterior surface of shaft working portion 18 are a plurality of at least two helical flutes 22. In the illustrated arrangement there are three spaced apart helical flutes 22. These helical flutes are formed into the exterior surface of the file working portion 18. Each helical flute has a flute surface 24. While three helical flutes 22 are illustrated, the file can be manufactured with only two flutes or can be manufactured with more than three flutes. As a practical consideration, however, the file is typically made with two or three flutes with three flutes being ideal. While four or more flutes could be employed, additional flutes serve to increase the complexity of manufacture without adding significantly to performance of the tool. Thus, for practical purposes, the ideal file construction that incorporates the principles of this invention will employ three flutes 22. These flutes provide therebetween three helical flanges 26.

Each of the helical flanges 26 has, at the outer end thereof, an end surface 28. Each end surface 28 contacts, in cross-sectional views, opposed flute surfaces 24. A continuous spiraled scraping/cutting edge 30 is formed at the outer end of each end surface 28, that is, where each end surface 28 contacts an opposed flute surface 24.

Each of the flange end surfaces 28 of FIG. 2 are arcuate, that is, each is formed of an arc that has a radius of curvature substantially equal to the basic radius of curvature of the shaft working portion in the area where the cross-sectional view of FIG. 2 is taken except that the rotational axis is offset relative to the longitudinal/rotational axis 20. In this way, each of the flange end surfaces 28 provides a scraping/cutting edge 30. This arrangement provides a small rake angle. That is, a tangent taken of flange end surface 28 at the scraping/cutting edge 30 departs only slightly from the tangent of the rotation of the shaft working portion at the area where the cross-sectional view of FIG. 2 is taken. In the embodiment of FIG. 2 each of the three flange end surfaces 28 are the same.

Figure 3:
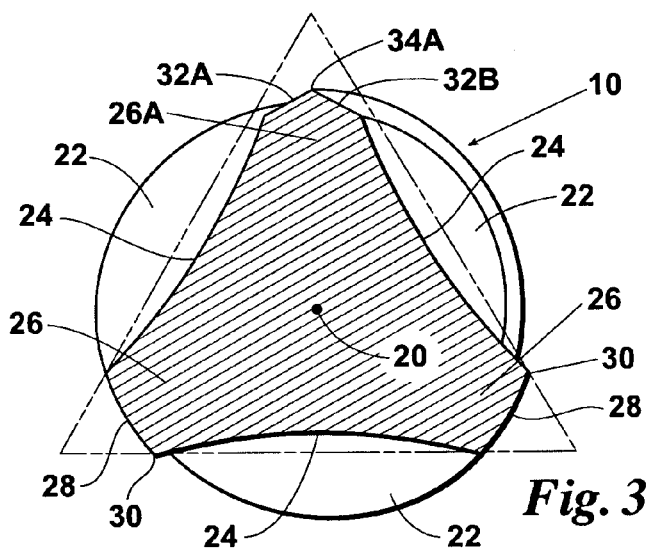
FIG. 3 is a cross-sectional view as in FIG. 2 but showing an alternate embodiment of the cross-sectional of the file providing more aggressive cutting/scraping action.

FIG. 3 is an alternate embodiment of FIG. 1 having essentially all of the same elements as indicated in FIG. 2 and differs only in that in FIG. 3 there are two arcuate flange end surfaces 28 each having a scraping/cutting edge 30, however, one of the flange portions 26 does not terminate in an arcuate end surface. Instead, in FIG. 3 flange 26A terminates in an outer end surface defined by intersecting planes 32A and 32B so that a scraping edge 34A is formed at the intersection of the planes 32A and 32B.

In the illustrated embodiment of FIG. 3 spiral scraping edge 34A extends at a radius from the longitudinal/rotational axis 20 essentially equal to the radius of scraping/cutting edges 30 as described with reference to FIG. 2. Scraping edge 34A has a different kind of scraping action than scraping/cutting edges 30. Typically, a file having the three spiraled cutting edges of FIG. 3 provide more aggressive, scraping cutting action than that of the embodiment of FIG. 2.

Figure 4:
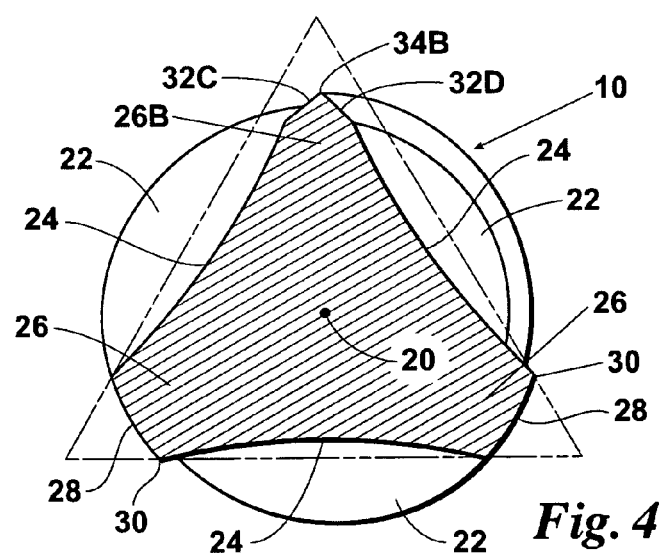
FIG. 4 is another alternate embodiment of the cross-sectional configuration of the endodontic file of FIG. 1 showing a cross-sectional arrangement that produces more aggressive cutting/scraping action than that of FIG. 2 or FIG. 3.

FIG. 4 is an alternate embodiment of FIG. 3 differing only in that flange 26B terminates at the outer end with planar end surfaces 32C and 32D. The only significant difference between the embodiment of FIG. 4 and that of FIG. 3 is that the planar end surfaces 32C and 32D of FIG. 4 intersect at a sharper angle than the end surfaces of 32A and 32B of FIG. 3. This forms a sharper spiraled cutting edge 34B that provides a more aggressive cutting/scraping edge and correspondingly a file having slightly different scraping/cutting action.

Figure 5:
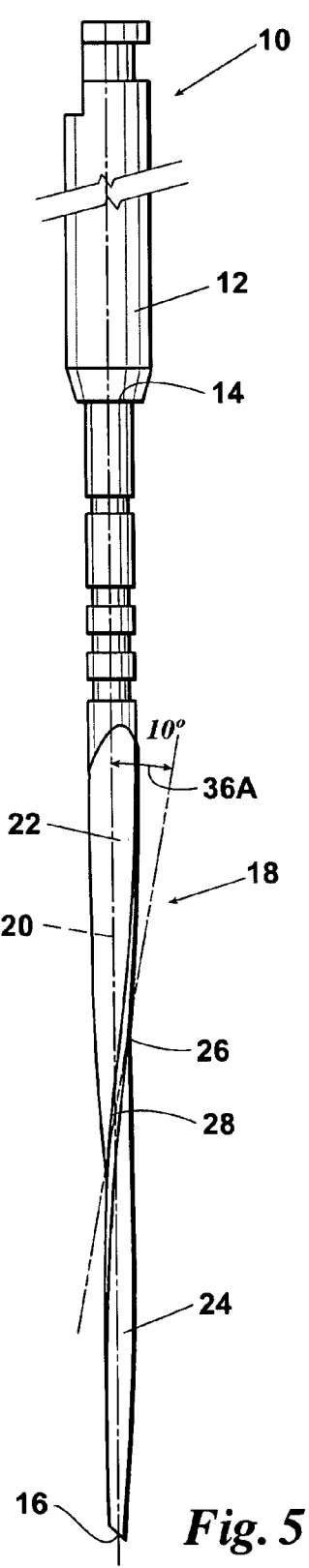
FIG. 5 is an elevational view of an endodontic file having a shank portion designed for rotational use in a hand piece as employed by an endodontist and showing an alternate configuration of the file working portion. In the embodiment of FIG. 5 a pair of equally spaced apart continuous concaved helical flutes are formed into the working portion, the helical flutes having a small, approximately 10° helical angle.

FIG. 5 is an embodiment of the endodontic file 10 as shown in FIG. 1 with a basic difference. That difference is a highly reduced helical angle. As shown in dotted outline in FIG. 5, the endodontic file has spiraled flutes 22 with spiraled flute surfaces 24 and with flanges 26 formed between the spiraled flutes. Each flange having an outer end surface 28. The difference of FIG. 5 and FIG. 1 is that in FIG. 5 the angle of the helical flange taken at a cross-section relative to the longitudinal axis 20 is very small. In the embodiment of FIG. 5 the angle of flange 26 with respect to a plane of the longitudinal/rotational axis 20 is approximately 10°.

Figure 6:
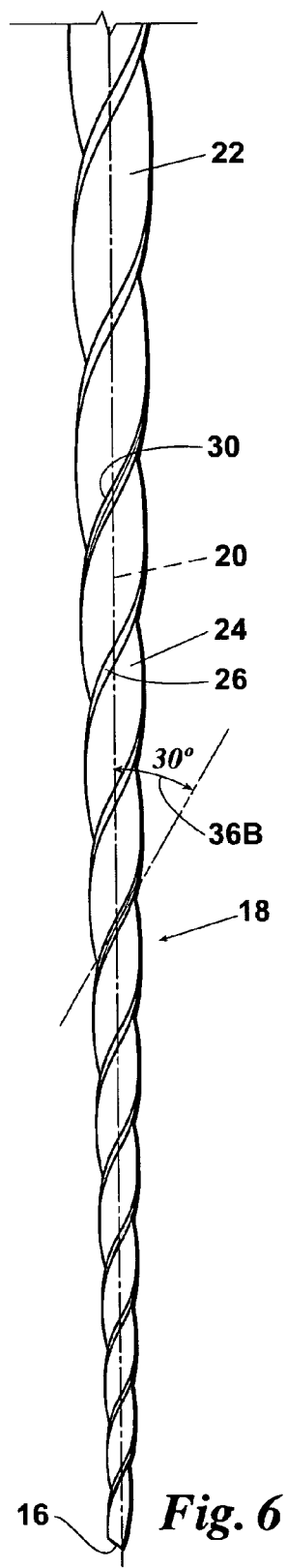
FIG. 6 shows part of a shaft working portion of an endodontic file and shows a plurality of helical flutes forming the working surface and wherein the helical flutes have an angle of 30° relative to a plane of the file longitudinal/rotational axis.
Figure 7:
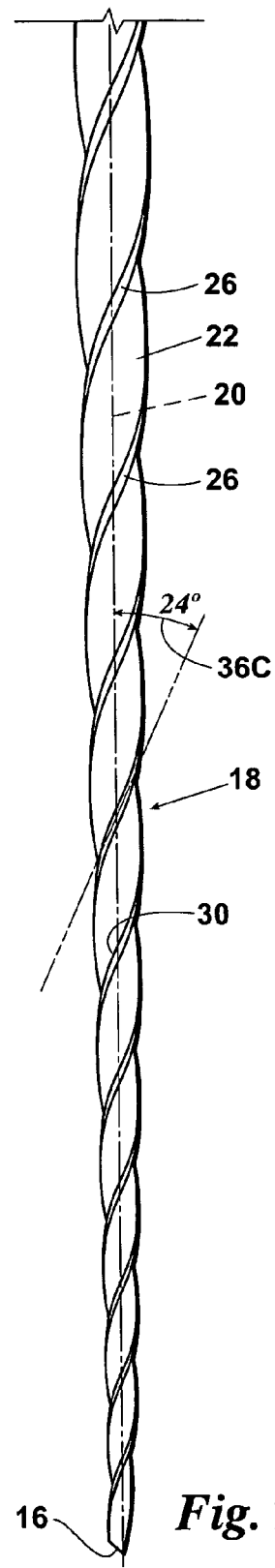
FIG. 7 shows the exterior shape of the working portion of an endodontic file as in FIG. 6 in which the working portion is defined by equally spaced apart continuous concaved helical flutes, the flutes having a helical angle of 24° relative to a plane of the longitudinal/rotational axis of the file.

FIGS. 6 through 9 each show an elevational view of a shaft working portion 18 of an endodontic file of the type shown in FIGS. 1 and 5. FIG. 6 illustrates the arrangement wherein the helical file flange has an angle with respect to a plane of the file longitudinal/rotational axis 20 of 30°. The helical angle in FIG. 5 of 10° can be contrasted with the helical angle of 30° in FIG. 6. While in FIG. 6 the helical angle 36B is 30°, in FIG. 7 the helical angle 36C is 24°. Thus FIGS. 5, 6 and 7 show that helical flutes and flanges can have highly selectable angles relative to a plane of a file longitudinal/rotational axis. The selected helical angle has a dramatic impact on the operation of a file as used in performing an endodontic procedure. Files having helical angles of 20° and greater tend to have a dramatic screwing action as they are rotated in a root canal. That is, they tend to thread toward the apical end of the root canal. On the other hand, files that have a small helical angle, such as less than 20°, do not have a strong screwing action but have a more pronounced scraping action. In performing an endodontic procedure, there are advantages to both screwing action and scraping action of a file. Scraping action tends to dislodge pulpal material and inwardly protruding portions of the root canal so as to clean and shape the root canal. However, scraping action is deficient if no provision is made for removing loosened material from within the root canal. That is, portions of the root canal wall must not only be scraped loose but must be removed. Screwing action of the file has a strong tendency to remove the dislodged material from within a root canal. Thus in selecting a helical angle for a file it is always a compromise between achieving good scraping action and achieving good removal action.

Further, the helical angle has a dramatic effect on the possibility of the file breaking off within the tooth. That is, a file that has a pronounced screwing action tends to thread deeper towards the apical area of the tooth and to become more quickly and easily stuck in a position within the tooth so that further rotation can cause the file to be twisted into broken pieces. Breaking a file in a root canal is always a serious matter. One of the important concepts of this invention is that advantages can be taken of the helical angle of the flanges so that the advantages of both higher helical angles and lower helical angles can be combined into a file.

FIG. 8 shows a portion of a shaft working portion, generally indicated by the numeral 18. This view shows the portion of the shaft that extends from approximately the lower half of the shaft working portion terminating in distal end 16. Shaft working portion 18 has, as with the previously described embodiment, spaced apart spiraled flutes 22 with flange portions 26 therebetween, each of the flanges providing a scraping/cutting edge 30. The illustrated working portion has a longitudinal/rotational axis 20. A unique feature of FIG. 8 is the provision wherein the helical angle 36D of one portion of the length of the file working portion is different from the helical angle 36E of a portion adjacent distal end 16.

The arrangement of FIG. 8 gives an endodontic file unique properties when being used to clean and shape a root canal. The upward portion having a helical angle 36D of 13° provides improved scraping action whereas the portion having a helical angle 36E of 17° adjacent distal end 16 has more threading action, tending to draw the file deeper into the root canal.

FIG. 9 shows a section of a shaft working portion as in FIG. 8 with the file having essentially the same base diameter and taper as FIG. 8 but wherein the portion adjacent distal end 16 has a helical angle 36F of 13°, with the working portion of the shaft farther displaced from distal end having a helical angle 36G of 17°. Thus, the arrangement of FIG. 9 provides a file wherein the portion of the working surface adjacent distal end 16 has a small helical angle and thereby provides more scraping action and less threading action as contrast with an intermediate portion of the working surface that has a helical angle of 17° providing increased threading action and reduced scraping action.

FIGS. 8 and 9 are indicative of the way the invention can be practiced by varying the helical angle along the length of a working portion of an endodontic shaft to minimize breakage, that is, to reduce the threading action of certain portions of the length of the shaft and increasing scraping action so that maximum effectiveness of the file can be achieved. In other words, the file can be arranged to most effectively clean and at the same time threadably remove debris from the interior of a root canal while minimizing the chance that the file will be subjected to increased torque resistance that could result in the file being twisted in two and leaving a portion of the file within the root canal.

While the invention has been described with a certain degree of particularity, it is manifest that many changes may be made in the details of construction and the arrangement of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

What is claimed is:

1. A rotatable endodontic file for cleaning/shaping a tooth root canal, comprising:

an elongated shaft having a proximal end portion, a distal end and a tapered working portion having a rotational axis, the working portion extending from said proximal portion to said distal end;

the external surface of said shaft working portion having a plurality of at least two spiraled, equally spaced apart continuous concaved helical flutes, the flutes having therebetween an equal number of spiraled, spaced apart flanges, each flange having in a plane perpendicular said rotational axis an outer end surface forming a continuous spiraled scraping/cutting edge extending the length of said shaft working portion, said flutes each having a helical angle as measured relative to said shaft rotational axis at each location along the length of said shaft working portion and wherein there are at least two different helical angles for each said flute and wherein the helical angles are proportionally unrelated to locations or diameters along the length of said working portion.

2. An endodontic file according to claim 1 wherein areas of said shaft working portion having flutes with a helical angle that produces increased threading action and reduced scraping action as said shaft is rotated and areas of said shaft working portion having flutes with a helical angle that produces decreased threading action and improved scraping action as said shaft is rotated.

3. An endodontic file according to claim 1 wherein a first area of said shaft working portion adjacent said proximal end portion has flutes with a selected helical angle and a second area of said shaft working portion adjacent said distal end has flutes with a second helical angle.

4. An endodontic file according to claim 1 wherein said outer end surface of each of said flanges has in one area a positive scraping/cutting edge and in another area a negative scraping/cutting edge.

5. A rotatable endodontic file according to claim 1 wherein each said flange outer end surface has a radius of curvature of the said shaft working portion.

6. A set of rotatable endodontic files for cleaning/shaping a tooth root canal, comprising:

a plurality of files each having an elongated shank having a proximal end portion, a distal end and a tapered working portion of a selected angle of taper and having a rotational axis extending from said proximal portion to said distal end;

the external surface of said shank working portion of each file having a plurality of at least two equally spaced apart continuous concaved helical flutes, the flutes having therebetween an equal number of spiraled, spaced apart flanges, each flange having in a plane perpendicular said rotational axis an outer end surface forming a continuous spiraled scraping/cutting edge extending the length of said shaft working portion, said flutes each having a helical angle as measured relative to said shaft rotational axis at each location along the length of said shaft working portion and wherein there are at least two different helical angles for each said flute, wherein the helical angles are proportionally unrelated to locations or diameters along the length of said working portion, and wherein each file in the set has essentially the same helical angles at selected locations and wherein each file in the set has a different diameter and/or taper.

7. A set of rotatable endodontic files according to claim 6, wherein at least one of said files in said set has a flange outer end surface having a radius of curvature of said shaft working portion.

\* \* \* \* \*